United States Patent
Cowe

(10) Patent No.: US 9,744,306 B2
(45) Date of Patent: Aug. 29, 2017

(54) INJECTION DEVICES

(75) Inventor: Toby Cowe, Oxford (GB)

(73) Assignee: OWEN MUMFORD LIMITED, Oxfordshire (GB)

(*) Notice: Subject to any disclaimer, the term of this patent is extended or adjusted under 35 U.S.C. 154(b) by 920 days.

(21) Appl. No.: 14/001,925

(22) PCT Filed: Mar. 2, 2012

(86) PCT No.: PCT/GB2012/050467
§ 371 (c)(1),
(2), (4) Date: Aug. 28, 2013

(87) PCT Pub. No.: WO2012/117252
PCT Pub. Date: Sep. 7, 2012

(65) Prior Publication Data
US 2013/0338601 A1 Dec. 19, 2013

Related U.S. Application Data

(60) Provisional application No. 61/448,410, filed on Mar. 2, 2011.

(30) Foreign Application Priority Data

Mar. 2, 2011 (GB) .................................. 1103558.1

(51) Int. Cl.
A61M 5/20 (2006.01)
A61M 5/315 (2006.01)

(52) U.S. Cl.
CPC ...... A61M 5/31535 (2013.01); A61M 5/2033 (2013.01); A61M 5/3157 (2013.01);
(Continued)

(58) Field of Classification Search
CPC ...... A61M 2005/202; A61M 2005/206; A61M 2005/208; A61M 2205/581;
(Continued)

(56) References Cited

U.S. PATENT DOCUMENTS 5,137,516 A * 8/1992 Rand .................... A61J 1/00
604/136
5,358,489 A * 10/1994 Wyrick ................ A61M 5/002
604/135

(Continued)

FOREIGN PATENT DOCUMENTS

EP 0 937 472 A2 8/1999
GB 2460398 A 2/2009
(Continued)

OTHER PUBLICATIONS

GB Search Report, dated Jun. 10, 2011, from corresponding GB application.
(Continued)

Primary Examiner — Gerald Landry, II
(74) Attorney, Agent, or Firm — Young & Thompson

(57) ABSTRACT

An injection device includes an injection complete indicator which includes its own bias and which is latched into a retracted position as the injection device is cocked. Upon firing the injection device, the injection complete indicator is kept in its retracted position until towards the end of the forward stroke of the drive mechanism, whereupon the injection complete indicator is unlatched and shoots forwardly under the influence of the bias to impact an abutment to generate an audible/tactile indication along with a visual indication.

19 Claims, 12 Drawing Sheets

(52) U.S. Cl.
CPC . *A61M 2005/202* (2013.01); *A61M 2005/206* (2013.01); *A61M 2005/208* (2013.01); *A61M 2205/581* (2013.01); *A61M 2205/582* (2013.01); *A61M 2205/583* (2013.01)

(58) Field of Classification Search
CPC ...... A61M 2205/582; A61M 2205/583; A61M 5/2033; A61M 5/3157
USPC .................................................. 604/135, 136
See application file for complete search history.

(56) References Cited

U.S. PATENT DOCUMENTS

| | | | |
|---|---|---|---|
| 5,637,094 A | 6/1997 | Stewart, Jr. et al. | |
| 6,099,503 A * | 8/2000 | Stradella | A61M 5/2033 604/131 |
| 6,454,743 B1 | 9/2002 | Weber | |
| 6,939,319 B1 * | 9/2005 | Anstead | A61M 5/30 604/68 |
| 2002/0120235 A1 * | 8/2002 | Enggaard | A61M 5/20 604/135 |
| 2002/0151839 A1 * | 10/2002 | Landau | A61M 5/30 604/68 |
| 2003/0105430 A1 * | 6/2003 | Lavi | A61M 5/2033 604/136 |
| 2005/0222539 A1 * | 10/2005 | Gonzales | A61M 5/2033 604/207 |
| 2006/0258990 A1 | 11/2006 | Weber | |
| 2006/0287630 A1 * | 12/2006 | Hommann | A61M 5/2033 604/130 |
| 2010/0063444 A1 * | 3/2010 | Wikner | A61M 5/2033 604/110 |
| 2010/0094214 A1 * | 4/2010 | Abry | A61M 5/20 604/110 |
| 2010/0137791 A1 * | 6/2010 | Plumptre | A61M 5/3146 604/68 |
| 2011/0054412 A1 * | 3/2011 | Eich | A61M 5/20 604/207 |
| 2011/0130723 A1 * | 6/2011 | Hirschel | A61M 5/2033 604/187 |
| 2011/0196311 A1 * | 8/2011 | Bicknell | A61M 5/2033 604/198 |
| 2012/0209192 A1 * | 8/2012 | Alexandersson | A61M 5/2033 604/135 |
| 2012/0296276 A1 * | 11/2012 | Nicholls | A61M 5/31501 604/110 |

FOREIGN PATENT DOCUMENTS

| | | |
|---|---|---|
| WO | 2004/108194 A1 | 12/2004 |
| WO | 2005/009515 A1 | 2/2005 |
| WO | 2005/009519 A1 | 2/2005 |
| WO | 2005/070481 A1 | 8/2005 |
| WO | 2007/132353 A2 | 11/2007 |
| WO | 2010035057 A1 | 4/2010 |

OTHER PUBLICATIONS

International Search Report, dated Jun. 15, 2012, from corresponding PCT application.

* cited by examiner

INJECTION DEVICES

BACKGROUND OF THE INVENTION

This invention relates to injection devices and in particular, but not exclusively, to reusable autoinjector devices comprising a housing into which a disposable syringe may be inserted to effect the injection and then removed and replaced as required for the next injection.

DESCRIPTION OF THE RELATED ART

It is a common requirement that autoinjectors signal to the user when the injection is complete by means of an 'injection complete' signal. The term 'injection complete' is used to refer to a condition in which a satisfactory delivery of the drug has been achieved. It is also desirable that this indication is not only visual but also audible and/or tactile, to provide confirmation to the user when injection site is out of sight, or would require some straining to see, for example in the buttocks or upper arm.

It is also desirable that the energy required to generate the audible or tactile signal does not subtract significant energy from the main drive source of the device as this might impair efficient sequencing and delivery. We have designed an injection device which provides an audible and/or tactile indication to the user as well as a visual indication, without taking significant energy from the main drive source. It is additionally desirable to provide an arrangement in which the indicator is reset automatically for each injection cycle.

SUMMARY OF THE INVENTION

Accordingly, in one aspect, this invention provides an injection device including an injection complete indicator for providing a kinetic impact indication, the device including:

a housing;

a plunger movable in said housing between cocked and fired positions under the influence of a plunger drive source;

an indicator element movable between an extended position and a retracted position and being biased towards said extended position by an indicator bias;

an indicator latch arrangement for latching said indicator element in a retracted position;

a motion transfer arrangement between the plunger and the indicator element for retracting said indicator element to said retracted position as said plunger is moved to its cocked position but allowing forward movement of said plunger relative to the indicator element;

the device being arranged such that, after firing, as the plunger nears or reaches the end of its operating stroke, it enables release of the indicator latch arrangement to cause the indicator element to move to its extended position under the influence of said bias to impact a stop surface to create said kinetic impact.

Preferably, said indicator element also provides a visual indication upon approaching or reaching its extended position.

It will be noted that the indicator element is provided with its own bias and that the motive force for moving the indicator forward after the indicator latch arrangement has been released may be provided by the indicator bias. Conveniently said motion transfer arrangement comprises an abutment surface associated with one of said plunger and said indicator element and a cooperating projection associated with the other thereof.

Preferably said indicator latch arrangement includes a flexible latch finger associated with said housing and having a latching tooth past which a flexible finger on the indicator element may snap as the indicator element is moved to its retracted position. The latch finger associated with the housing is advantageously resiliently deflectable to allow said indicator finger to move forwardly, with the deflection being prevented except when the plunger is at or near the end of its stroke. Once deflection is possible the indicator may be released for forward movement.

In many configurations the plunger is movable longitudinally between its cocked and fired positions, and the body finger preferably extends generally longitudinally, with the plunger having a support surface which underlies the body finger, until the plunger nears or reaches the end of its stroke.

Concurrently the latch tooth comprises respective ramp surfaces facing in the cocking and firing directions respectively, with the ramp surfaces providing a profile in which the inclination of the ramp face first contacted by the indicator finger when moving to its retracted position is shallower than the other face, whereby the indicator finger can snap past the latch tooth when moving in the direction of retraction, but not in the opposite direction.

In another aspect, this invention provides an injection device including an injection complete indicator, the device including:

a housing;

a plunger movable in said housing between cocked and fired positions under the influence of a plunger drive source;

an indicator element movable between a pre-firing position and an injection complete position;

the device being arranged such that, after firing, as the plunger nears or reaches the end of its operating stroke, the indicator element is caused to move to its injection complete position and wherein subsequent re-cocking of the plunger returns said indicator element to its pre-firing position.

BRIEF DESCRIPTION OF THE DRAWING FIGURES

Whilst the invention has been described above, it extends to any novel combination of the features set out above, or in the following description or drawings. Whilst the invention may be performed in various ways, an embodiment thereof will now be described by way of example only, reference being made to the accompanying drawings in which:

FIGS. 1(a) to (e) are perspective views of an autoinjection device in accordance with this invention showing various stages in operation prior to, during and after firing;

Figure 1:
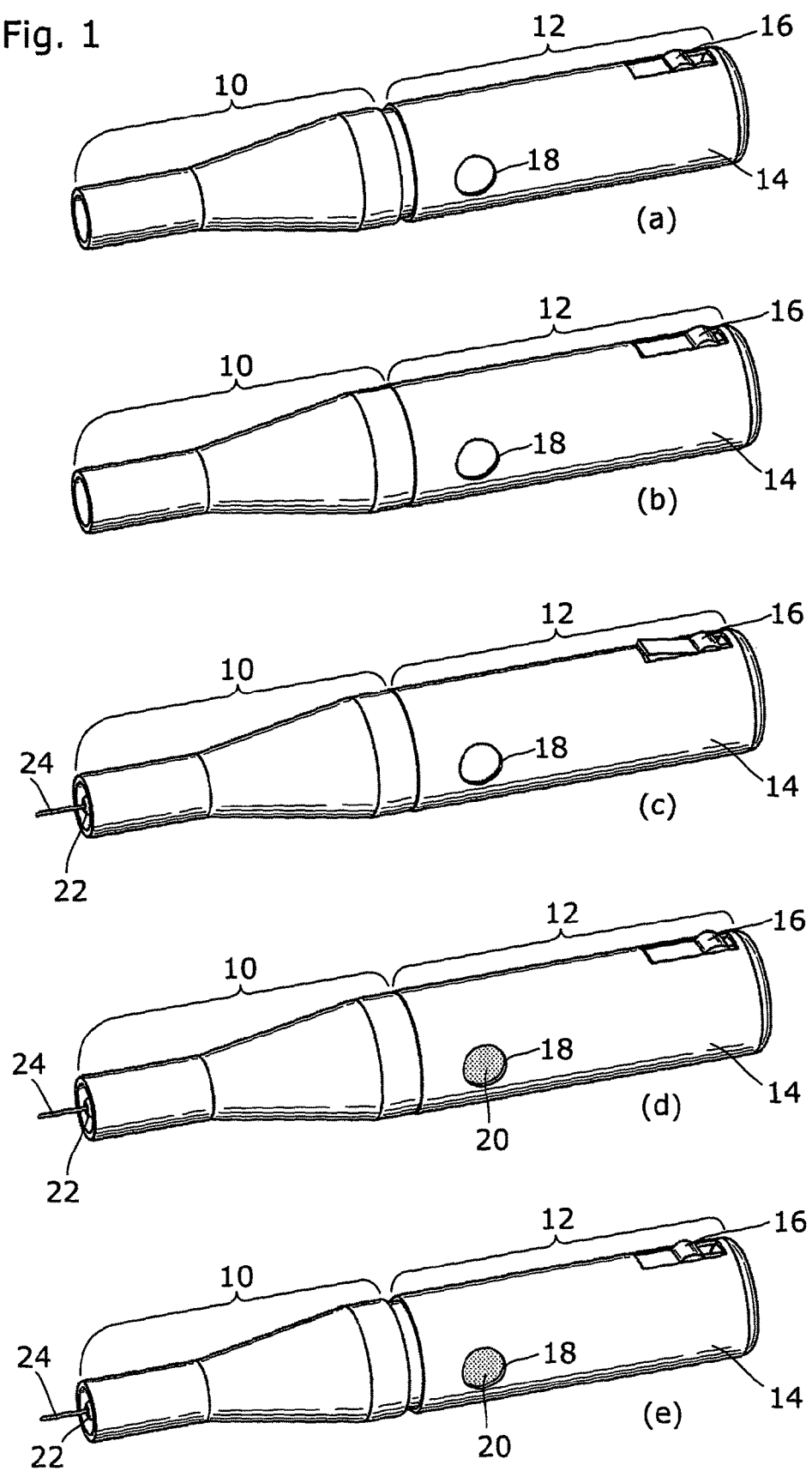
Figure 2:
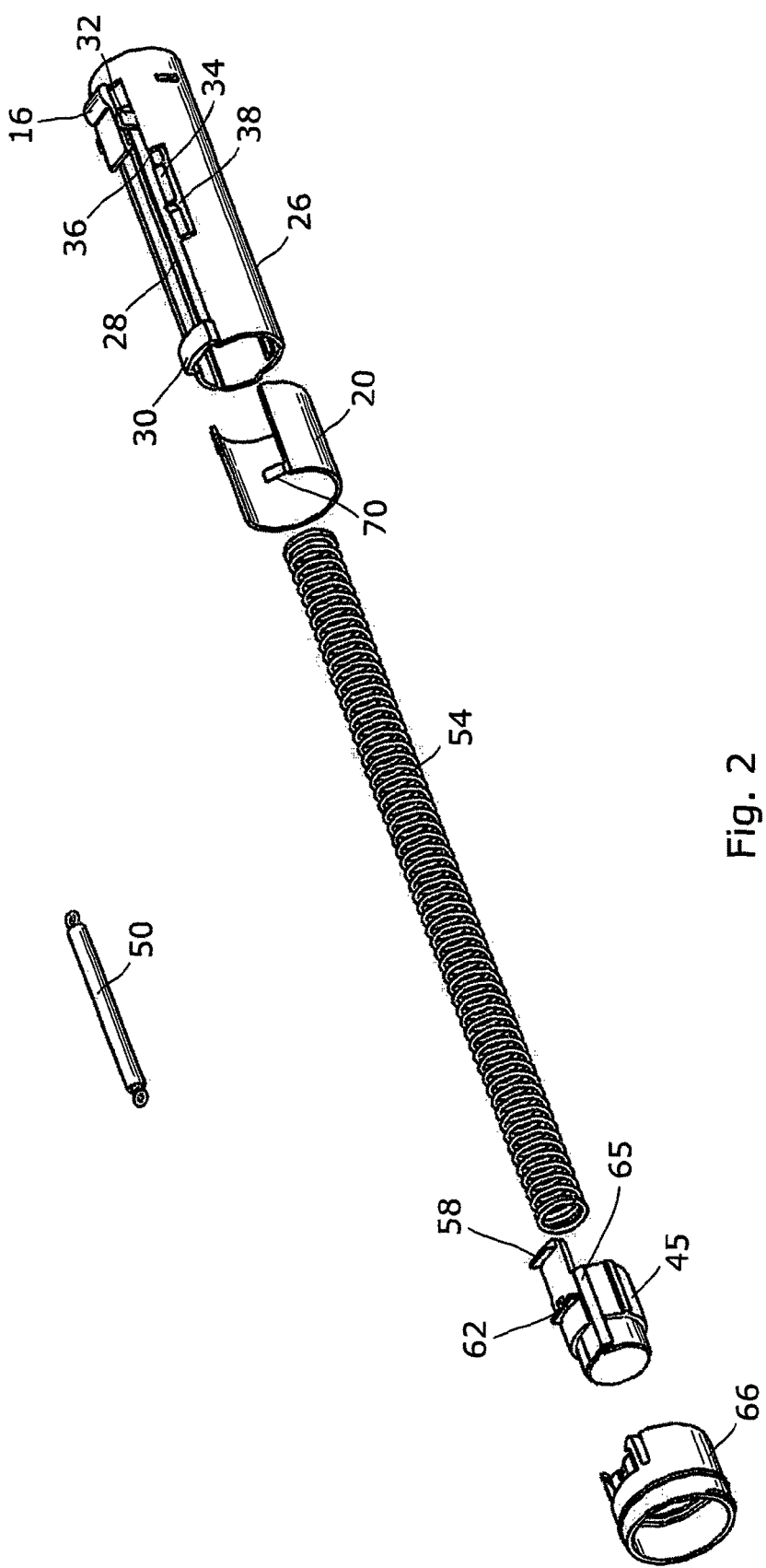
FIG. 2 is an exploded view of the rear body assembly excluding the cover.
Figure 3:
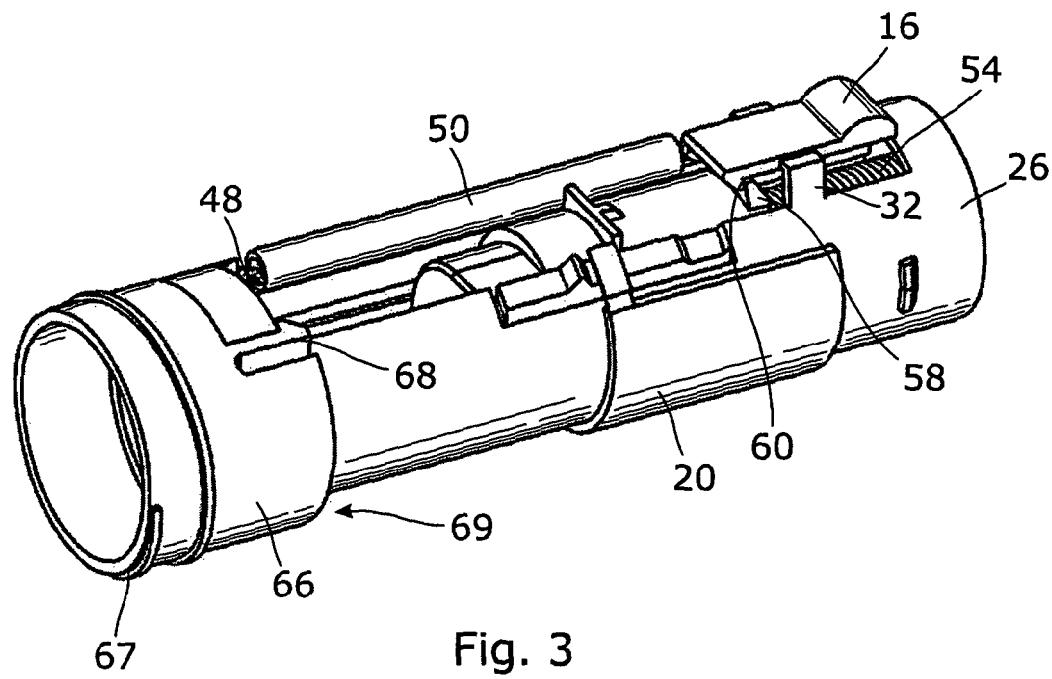
FIG. 3 is a view of the rear body assembly of the embodiment of FIG. 1, with the cover removed.
Figure 4:
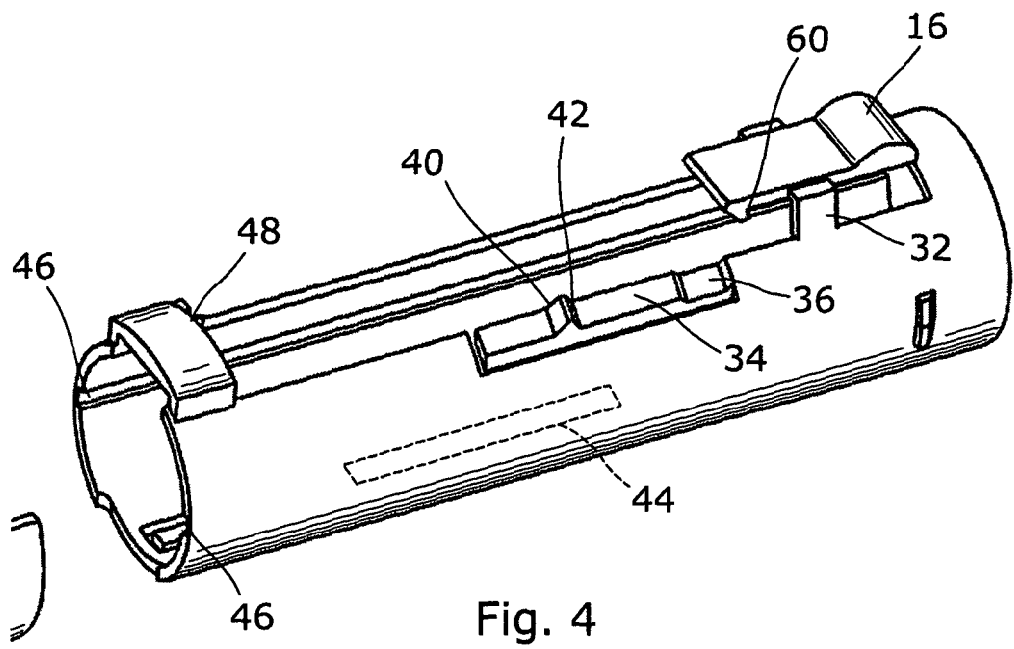
FIG. 4 is a perspective view of the rear body housing of the rear body assembly.
Figure 5:
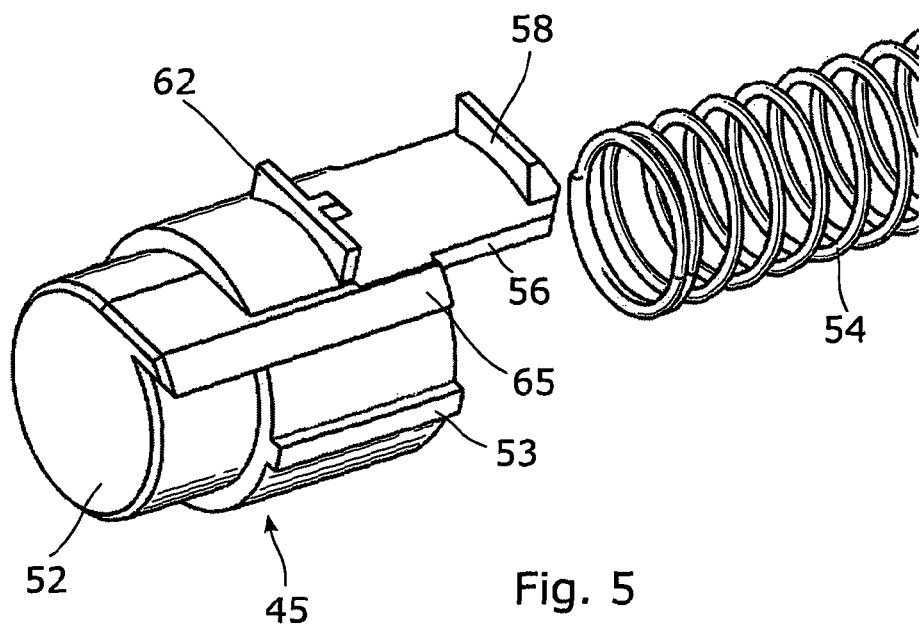
FIG. 5 is a perspective view of the indicator and forward end of the rear body housing.
Figure 6:
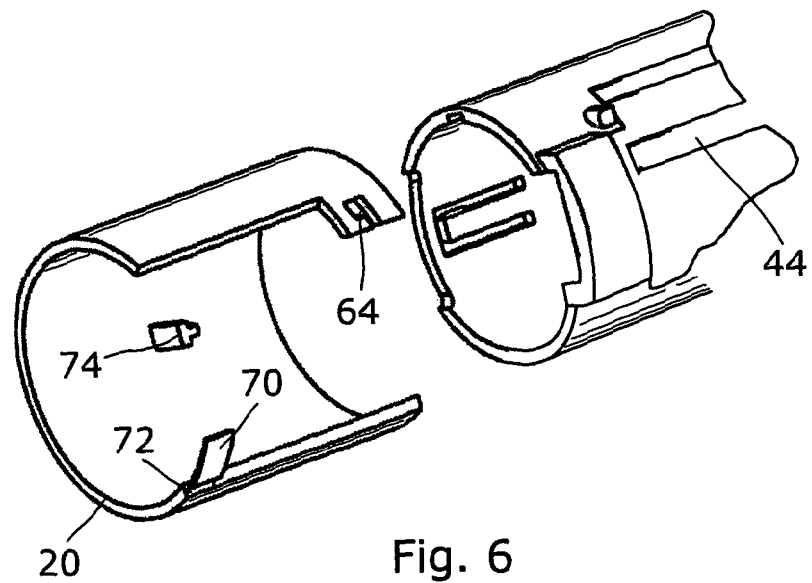
FIG. 6 is a perspective view of the plunger and part of the drive spring of the rear body assembly.

FIGS. 7(a) to (h) are perspective views of the rear body assembly showing the configuration of the various components in sequence through a cocking and firing operation, and FIGS. 8(a) to (h) are corresponding side views of the rear assembly during these operations.

DETAILED DESCRIPTION OF THE INVENTION

Referring initially to FIGS. 1(a) to (e), a preferred embodiment of autoinjector comprises a separable body comprising a front body assembly 10 screwed or otherwise releasably coupled to a rear body 12 having an outer slideable cover 14. The device is designed to be reusable with the user separating the front and rear body assemblies, inserting or replacing a syringe 22 housed in the front body assembly, priming or cocking a drive mechanism contained in the rear body assembly, and connecting the front and rear body assemblies together. This is similar to our well known Autoject® II device and as described in WO2004/108194. As in the arrangement of WO2004/108194, the cover 14 is biased rearwardly to a position where it interlocks with a trigger 16 to prevent actuation thereof. The cover 14 also has a window 18 through which an indicator sleeve 20 becomes visible upon satisfactory completion of an injection (see FIG. 1(d)). In order to operate the device, the operator grasps the cover 14 and presses the front end of the front body assembly 10 against the injection site, thus shifting the cover 14 forwardly to release the mechanical interlock. On pressing the trigger 16, the drive mechanism inside the rear body housing moves a plunger forwardly which initially advances the syringe 22 so that its needle 24 penetrates the injection site and thereafter the plunger moves the syringe piston to expel a dose. Upon nearing or reaching the forward end of its stroke, the plunger releases the indicator sleeve 20 which shoots forward to become visible to give a visual indication in window 18 and also to impact an internal surface to create an audible and tactile signal (FIG. 1(d)). On removing the device from the injection site the reaction force is removed and so the cover 14 again shifts rearwardly on the rear body to interlock with the trigger 16.

Referring initially to FIGS. 2 to 6, the rear body assembly 12 comprises a rear body housing 26 of generally cylindrical form cut away on its upper surface to provide an open wide slot 28 bridged at its forward end by a bridge 30 and supporting the trigger 16 at its rear end by means of live hinges 32. About half way down the slot 28 extends a parallel axial finger 34 hinged at its rear end by a live hinge 36 so that it can deflect resiliently into the bore of the rear body housing 26. The axial finger 34 has an asymmetric latch tooth 38 having a shallowly inclined forward ramp face 40 and a steeper rear ramp face 42. In the base of the rear body housing 26, opposite the wide slot 28 is a narrow slot 44 which allows a lost motion connection between the indicator sleeve 20 and the plunger 45 as to be described below. At 90° to the slots 28 and 44 are disposed internal guide grooves 46 that constrain the plunger so that it moves longitudinally without rotational movement. The bridge 30 includes an anchorage 48 for one end of an indicator spring 50.

The plunger is generally of stepped cylindrical form having a flat front end face 52 for engaging the syringe plunger (not shown) and open at its rear end to receive the front end of a drive spring 54. Side ribs 53 run in the guide grooves 46 of the rear body housing. Extending rearwardly from the upper side of the plunger as viewed is a tab 56 having a latch rib 58 which cooperates with a complementary latch rib 60 on the trigger 16 when the plunger is in its cocked position. A stop 62 upstands from a forward region of the tab 56 and cooperates with the bridge 30 on the rear body housing 26 to limit forward movement of the plunger. Extending along the entire length of the main plunger body 45 is a part cylindrical support surface 65 which cooperates with the latch finger 34 to prevent inward resilient deflection of the axial finger 34 until the plunger is at or near its forwardmost position.

Figure 7A:
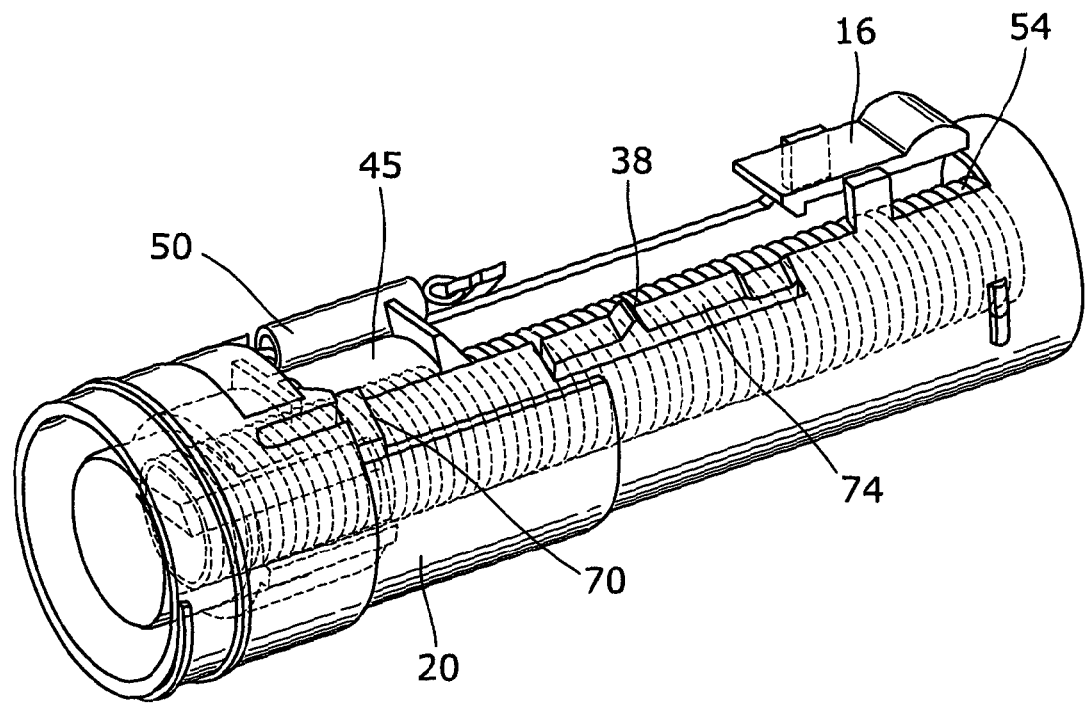
Figure 8A:
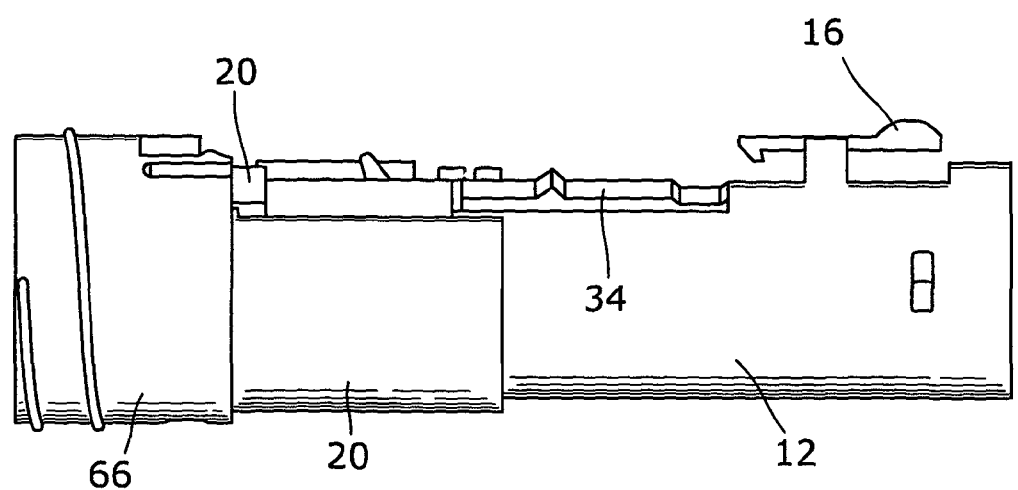
Figure 7B:
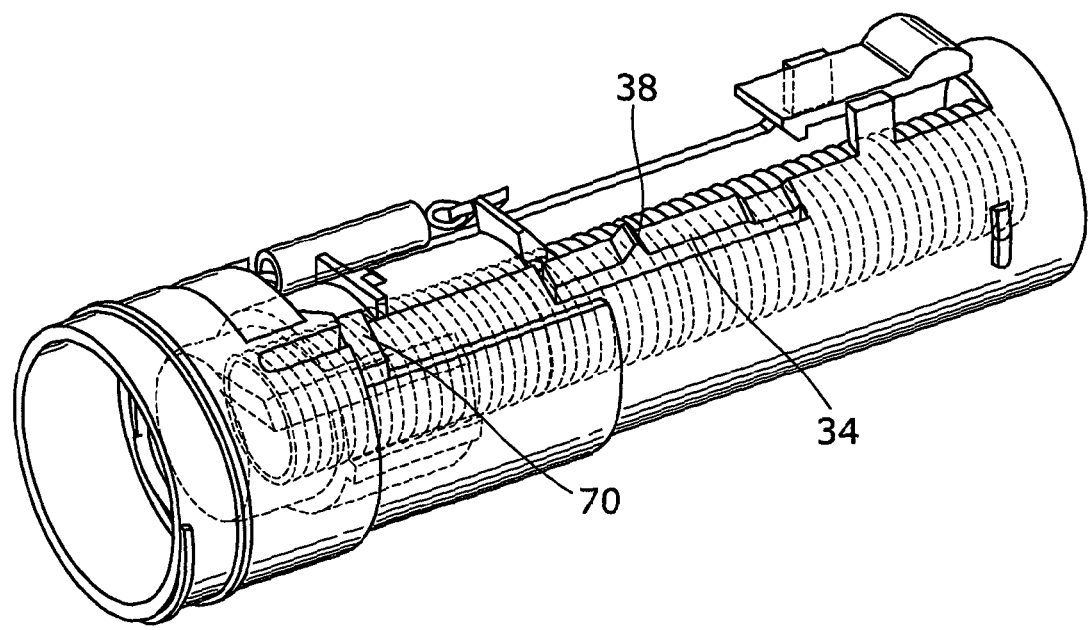
Figure 8B:
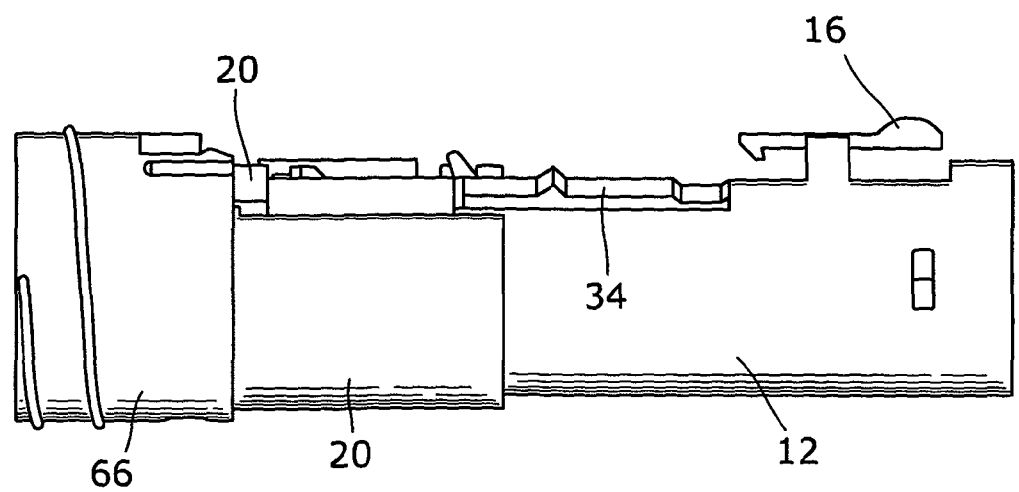
Figure 7C:
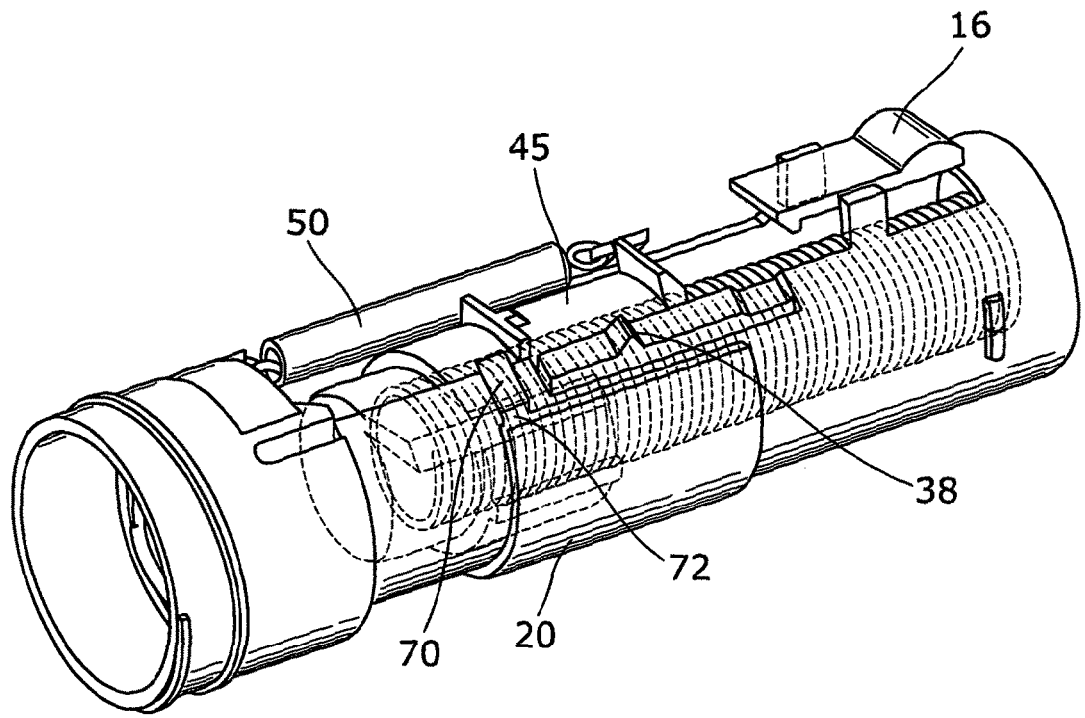
Figure 8C:
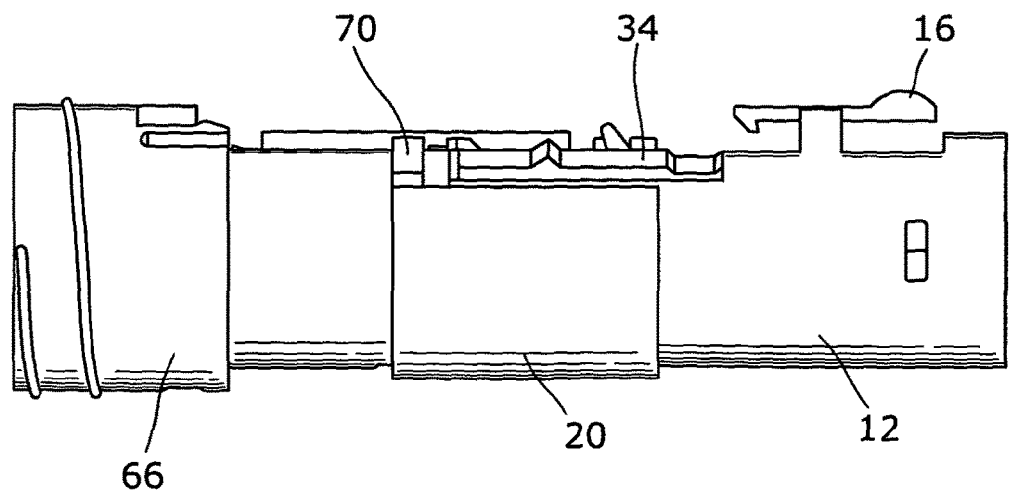
Figure 7D:
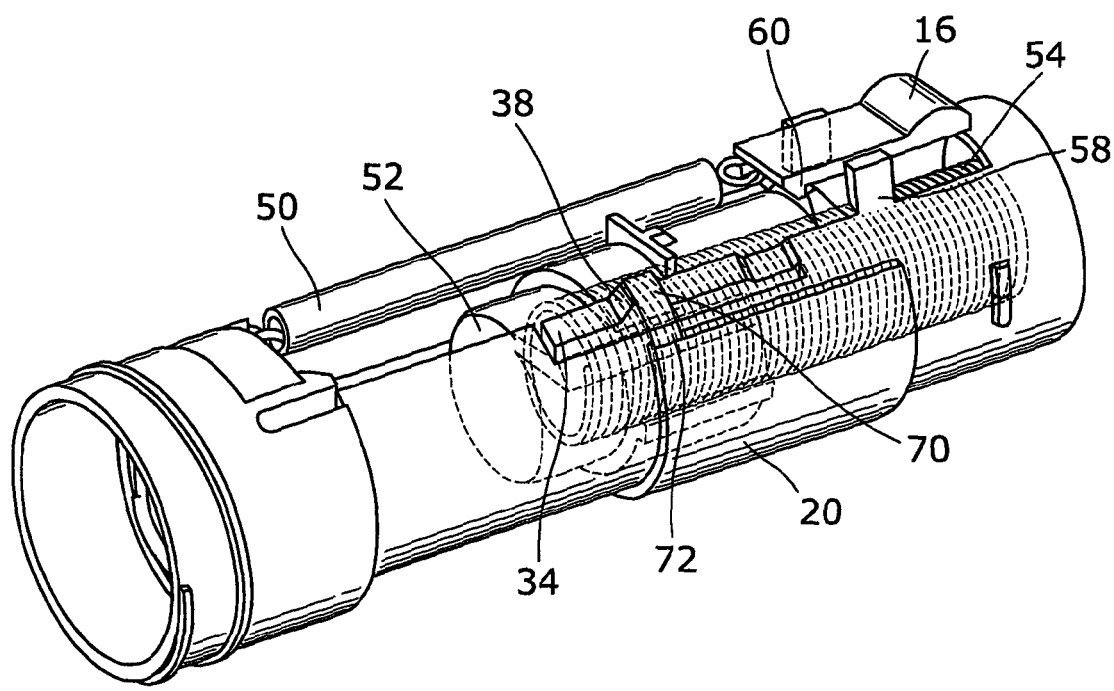
Figure 8D:
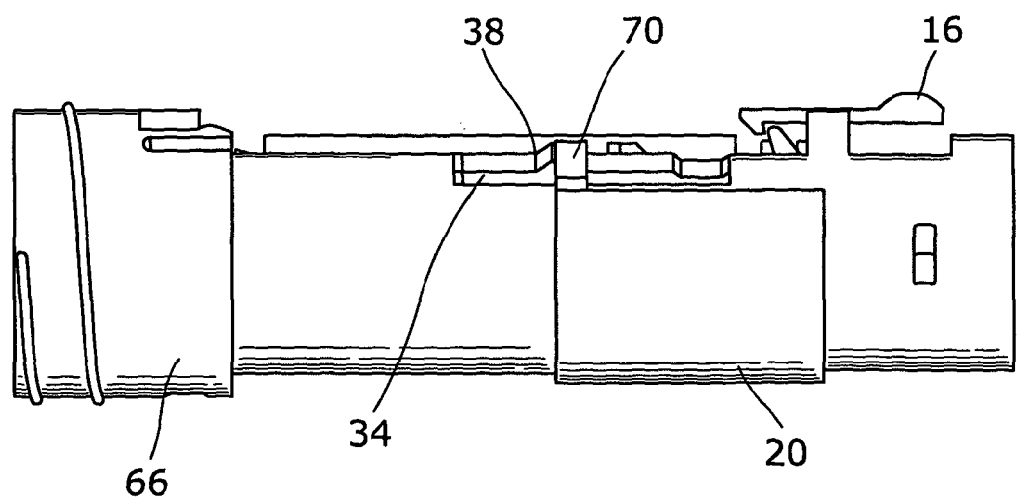
Figure 7E:
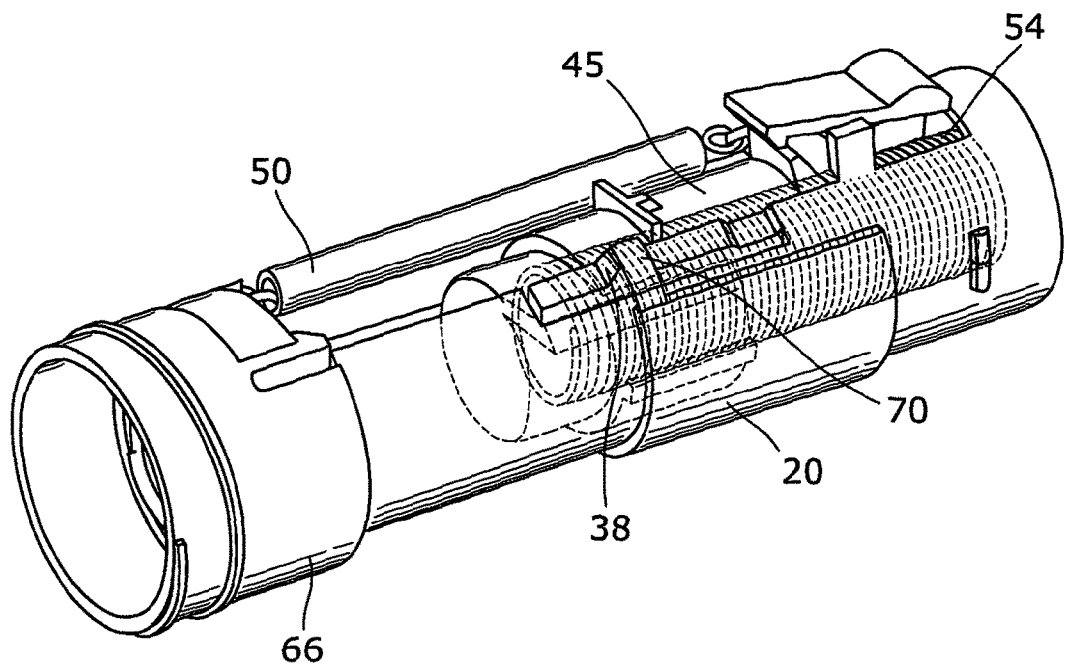
Figure 8E:
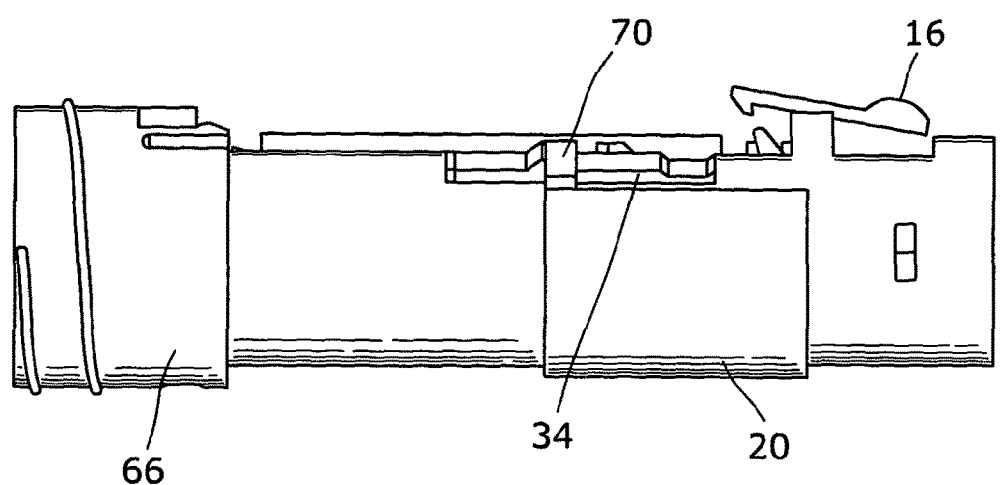
Figure 7F:
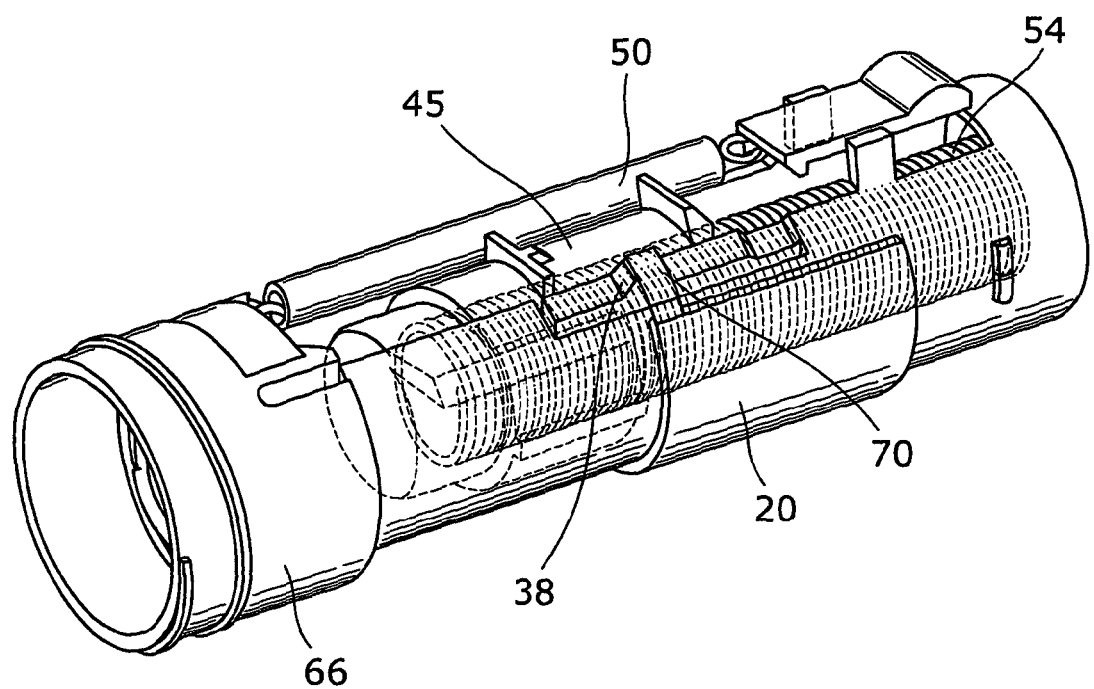
Figure 8F:
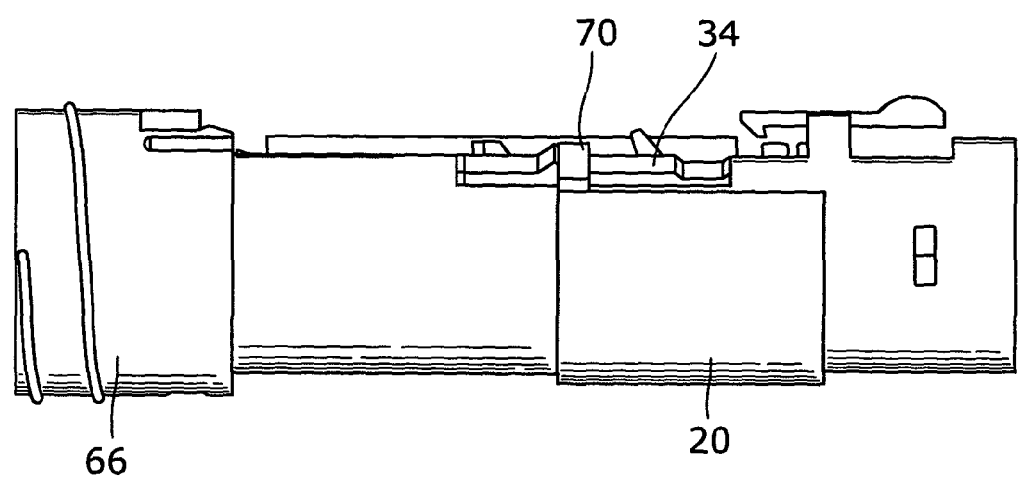
Figure 7G:
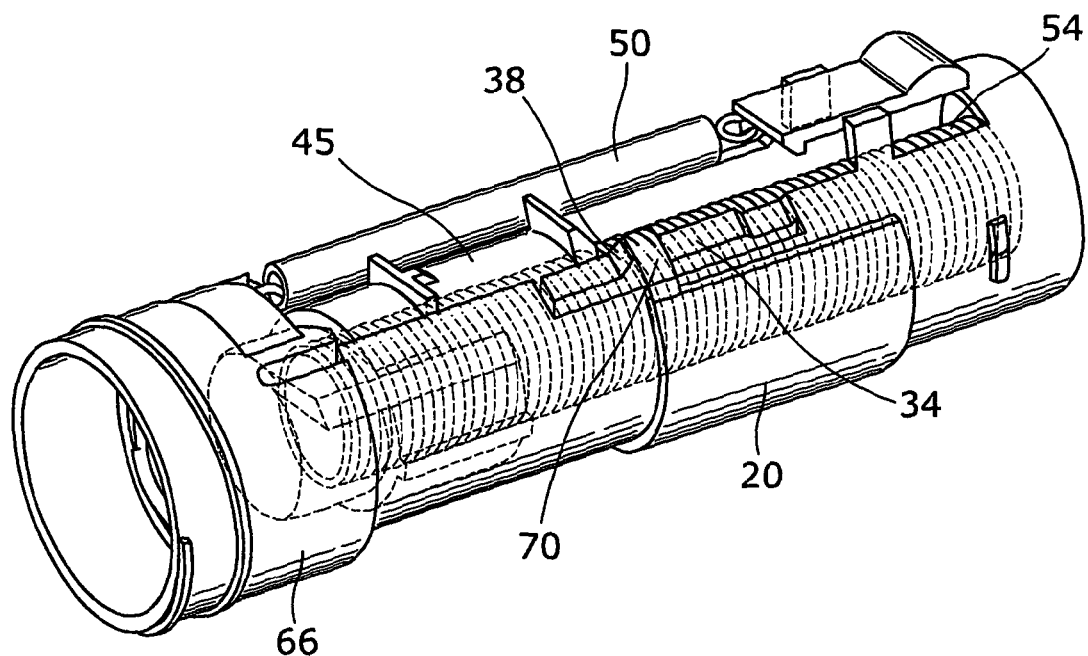
Figure 8G:
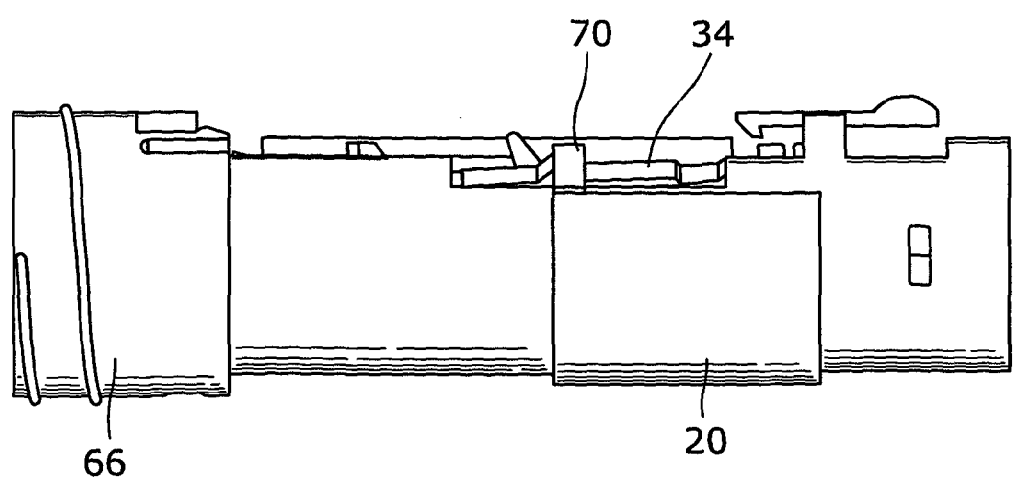
Figure 7H:
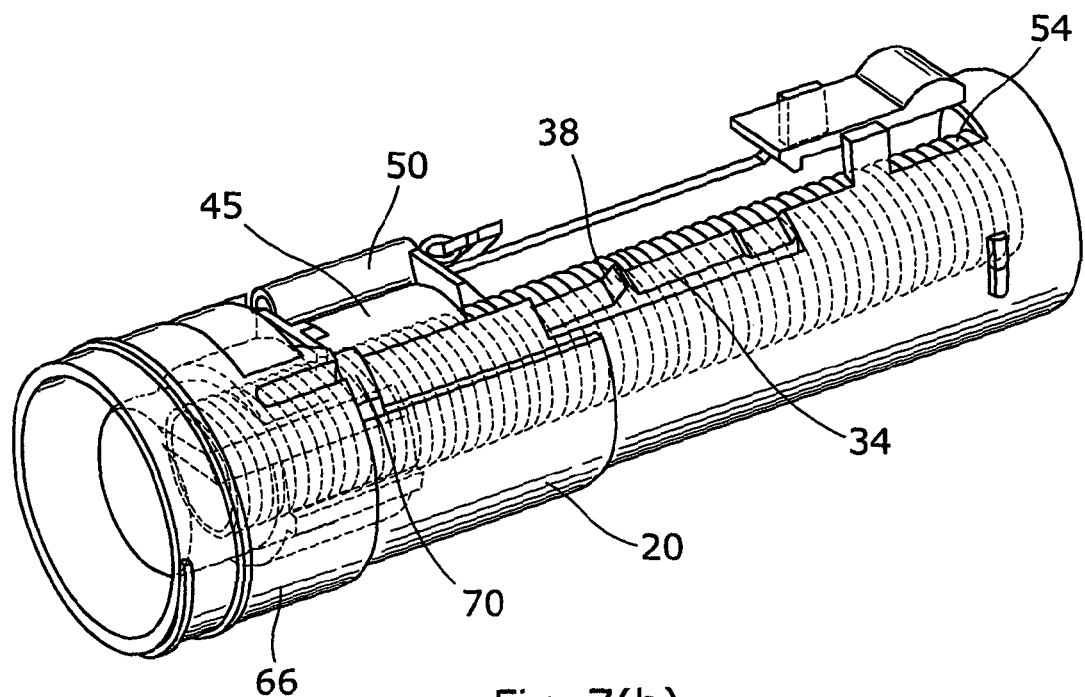
Figure 8H:
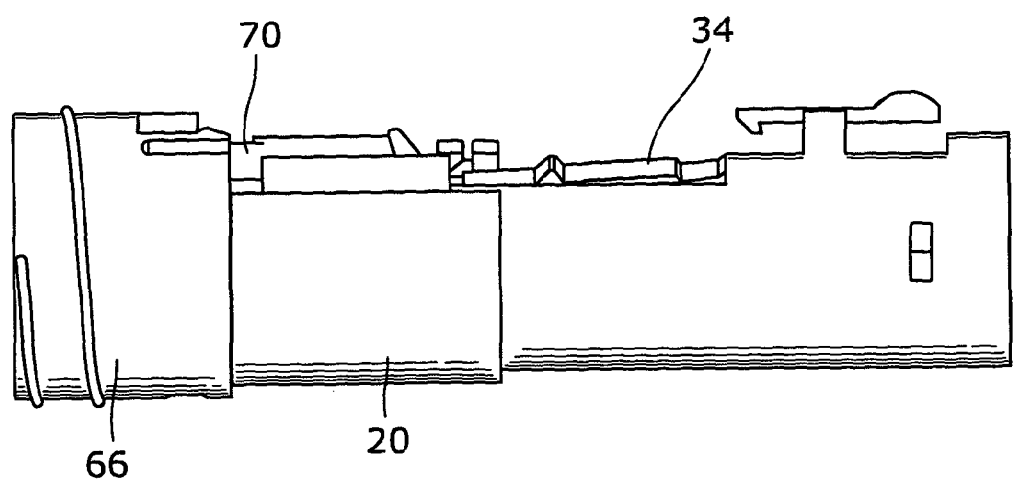

The indicator sleeve 20 is slideably mounted around the outside of the rear body housing 26 for movement between the forwardmost, indicating, position shown in FIGS. 7(a) and 8(a) to the retracted position shown in FIGS. 7(d) and 8(d). The indicator 20 is biased forwardly by means of the indicator spring 50 which is a tension spring. The indicator spring 50 is connected to the indicator 20 at a spring anchorage 64.

A collar fitting 66 clips to the front end of the rear body housing 26 by means of sprung arms 68 which clip around the bridge 30. The collar fitting provides an annular stop surface 69 (see FIG. 3) which limits forward movement of the indicator sleeve 20 and also acts as an impact surface to generate an audible/tactile signal. The collar fitting 66 also includes a thread 67 to allow the rear body assembly to be screwed to the front body assembly 10.

The indicator sleeve 20 is cut away on its upper surface to leave a cutaway region at the forward end of which is a circumferential finger 70 resiliently attached by a live hinge 72 to the indicator sleeve 20. The circumferential finger 70 cooperates with the latch tooth 38 on the axial finger 34 of the rear body assembly in a manner to be described below. Opposite the cutaway region and projecting inwardly from the inner wall of the indicator is a projection 74 which extends through the narrow slot 44 in the base of the rear body assembly 26 to project into the path of the rear of the plunger as it is moved rearwardly to cock the device.

Referring now more particularly to the sequence shown in FIGS. 7(a) to (h) and 8(a) to (h), FIG. 7(a) shows the various components of the rear body assembly in the configuration prior to cocking. The indicator sleeve 20 and the plunger 45 are at their forwardmost positions with the indicator spring 50 and main drive springs 54 in relatively relaxed conditions. In order to cock the device, the front end of the front body assembly 10 (or any other suitable tool) is placed against the front end face 52 of the plunger to urge the plunger rearwardly. As the plunger moves rearwardly, the main drive spring 54 is compressed (FIGS. 7(b) and 8(b)). After a small amount of rearward movement, the rearward surface of the plunger contacts the projection 74 on the indicator sleeve 20 so that the two move rearwardly together (FIGS. 7(c) and 8(c)). At this point, the support surface 65 on the plunger 45 is underlying the axial finger 34 thereby preventing it from resilient inward movement. Further rearward movement of the plunger 45 carries the indicator sleeve 20 with it so that the circumferential finger 70 engages the shallow inclined forward facing ramp surface 40 on the latch tooth 38 so as to snap past it (FIGS. 7(d) and 8(d)). The force of the extended indicator spring 50, the ramp angle of the steep rearward ramp face 42 and the flexibility of the live hinge 72 are selected such that the tension spring is not strong enough to pull the circumferential finger 70 back past the latch tooth 38 when the axial finger 34 is held against inward deflection.

In this position, the latch rib 58 on the plunger has snapped past the latch rib 60 on the trigger 16 thereby cocking the plunger and restraining it against movement, with the drive spring 54 compressed.

The rear assembly is now in a cocked position ready for firing and the device can be assembled by loading a syringe into the front body portion and screwing it onto the rear body portion. To fire the device, the trigger 16 is depressed, releasing the plunger 45 for forward movement (FIGS. 7(e) and 8(e)). The plunger 45 then moves forwardly to extend the syringe and, during all but the last part of the stroke of movement of the piston, the support surface 65 thereon underlies the axial finger 34 and prevents it from displacing inwardly and so the indicator sleeve 20 is held in its rearmost position (see FIGS. 7(*f*) and (*g*)). But in the final part of the stroke the plunger 45 is in a position where the support surface 62 is forwardly of the axial finger, no longer supporting it, so that the circumferential finger 70 on the indicator sleeve may cam the axial finger 34 downwardly, releasing the indicator sleeve to shoot forwards to impact the collar fitting 66, emitting an audible and tactile signal as the forward facing circumferential edge on the indicator element strikes a corresponding rearward surface on the collar fitting 66, and also making the indicator visible behind window 18 of the cover 14.

In this manner, audible, visual and tactile indications of end of dose are provided for the user without significantly diverting the energy of the main drive spring 54. Also the indicator is reset automatically each time the device is locked.

The invention claimed is:

1. An injection device including an injection complete indicator for providing a kinetic impact indication, the injection device further including:
   a housing (26);
   a plunger (45) having an operating stroke and movable in said housing between a cocked position and a fired position;
   a drive mechanism including:
      a plunger drive source (54) for moving the plunger between the cocked position and the fired position,
      a latch for holding the plunger in the cocked position against the plunger drive source, and
      a trigger for releasing the latch such that the plunger is moved from the cocked position to the fired position under the influence of the plunger drive source;
   an indicator, comprising:
      an indicator element (20) movable between an extended position and a retracted position,
      an indicator bias (50) configured to bias said indicator element (20) towards said extended position,
      an indicator latch arrangement (70,34) for latching said indicator element (20) in a retracted position against said indicator bias (50), and
      a motion transfer arrangement (74) between the plunger and the indicator element for retracting said indicator element (20) against the indicator bias (50) to said retracted position as said plunger (45) is moved to the cocked position but allowing forward movement of said plunger relative to the indicator element,
   wherein the device is arranged such that, after firing, as the plunger (45) nears or reaches the end of the operating stroke, it enables release of the indicator latch arrangement (70,34) to cause the indicator element (20) to move to the extended position under the influence of said indicator bias (50) to impact a stop surface to create said kinetic impact.

2. An injection device according to claim 1, wherein said motion transfer arrangement comprises an abutment surface associated with one of said plunger (45) and said indicator element (20) and a cooperating projection (74) associated with the other thereof.

3. An injection device according to claim 1, wherein said indicator latch arrangement includes a flexible latch finger (34) associated with said housing and having a latching tooth (38) past which a flexible finger (70) on the indicator element (20) may snap past as the indicator element is moved to the retracted position.

4. An injection device according to claim 3, wherein the latch finger (34) associated with the housing is resiliently deflectable to allow said flexible finger (70) to move forwardly, with the deflection being prevented except when the plunger is at or near the end of the operating stroke.

5. An injection device according to claim 4, wherein the plunger (45) is movable longitudinally between the cocked and fired positions, and the latch finger (34) extends generally longitudinally, with the plunger (45) having a support surface (62) which underlies the latch finger (34), until the plunger nears or reaches the end of the operating stroke.

6. An injection device according to claim 3, wherein the latch tooth (38) comprises respective ramp surfaces facing in the cocking and firing directions respectively, with the ramp surfaces providing a profile in which the inclination of the ramp face first contacted by the flexible finger when moving to the retracted position is shallower than the other face, whereby the flexible finger can snap past the latch tooth when moving in the direction of retraction, but not in the opposite direction.

7. An injection device according to claim 1, wherein said indicator element also provides a visual indication on approaching or arriving at said extended position.

8. An injection device according to claim 1, wherein the indicator element (20) comprises an element slideably mounted with respect to said housing.

9. An injection device according to claim 8, wherein said indicator element is provided with a forward facing edge adapted to impact a rearward facing surface associated with said housing (20).

10. An injection device according to claim 2, wherein said indicator latch arrangement includes a flexible latch finger (34) associated with said housing and having a latching tooth (38) past which a flexible finger (70) on the indicator element (20) may snap past as the indicator element is moved to the retracted position.

11. An injection device according to claim 4, wherein the latch tooth (38) comprises respective ramp surfaces facing in the cocking and firing directions respectively, with the ramp surfaces providing a profile in which the inclination of the ramp face first contacted by the flexible finger when moving to the retracted position is shallower than the other face, whereby the flexible finger can snap past the latch tooth when moving in the direction of retraction, but not in the opposite direction.

12. An injection device according to claim 5, wherein the latch tooth (38) comprises respective ramp surfaces facing in the cocking and firing directions respectively, with the ramp surfaces providing a profile in which the inclination of the ramp face first contacted by the flexible finger when moving to the retracted position is shallower than the other face, whereby the flexible finger can snap past the latch tooth when moving in the direction of retraction, but not in the opposite direction.

13. An injection device according to claim 2, wherein said indicator element also provides a visual indication on approaching or arriving at said extended position.

14. An injection device according to claim 3, wherein said indicator element also provides a visual indication on approaching or arriving at said extended position.

15. An injection device according to claim 4, wherein said indicator element also provides a visual indication on approaching or arriving at said extended position.

16. An injection device according to claim 5, wherein said indicator element also provides a visual indication on approaching or arriving at said extended position.

17. An injection device according to claim 6, wherein said indicator element also provides a visual indication on approaching or arriving at said extended position.

18. An injection device according to claim 2, wherein the indicator element (20) comprises an element slideably mounted with respect to said housing.

19. An injection device according to claim 3, wherein the indicator element (20) comprises an element slideably mounted with respect to said housing.

* * * * *